United States Patent [19]

Hoey

[11] 4,225,725

[45] Sep. 30, 1980

[54] LOWER ALKOXYMETHYL ESTERS OF 2,4,6-TRIIODOBENZOIC ACID DERIVATIVES

[75] Inventor: George B. Hoey, Ferguson, Mo.

[73] Assignee: Mallinckrodt, Inc., St. Louis, Mo.

[21] Appl. No.: 624,011

[22] Filed: Oct. 20, 1975

[51] Int. Cl.[2] .................. C07C 103/46; C07C 103/76; C07C 103/84

[52] U.S. Cl. ...................................... 560/37; 424/180; 424/309; 424/310; 536/4; 560/12; 560/13; 560/34; 560/41; 560/43; 560/45; 560/47; 560/65

[58] Field of Search ............... 260/471 R; 560/43, 47, 560/37

[56] References Cited

U.S. PATENT DOCUMENTS

| | | | |
|---|---|---|---|
| 3,097,228 | 7/1963 | Larsen | 560/47 |
| 3,119,858 | 1/1964 | Larsen | 260/471 R |
| 3,144,479 | 8/1964 | Herrmann | 560/47 |
| 3,484,481 | 12/1969 | Obendorf | 260/471 R |
| 3,795,698 | 3/1974 | Soulal et al. | 260/471 R |
| 4,001,298 | 1/1977 | Gries et al. | 260/471 R |

FOREIGN PATENT DOCUMENTS

| | | |
|---|---|---|
| 1082368 | 5/1960 | Fed. Rep. of Germany . |
| 869083 | 5/1961 | United Kingdom . |
| 961902 | 6/1964 | United Kingdom . |

*Primary Examiner*—Vivian Garner
*Attorney, Agent, or Firm*—Roy J. Klostermann

[57] ABSTRACT

Esters of certain 2,4,6-triiodobenzoic acid derivatives are useful as X-Ray contrast media. Representative compounds are the ethoxymethyl esters of acetrizoic, iothalamic and iodobenzamic acids.

4 Claims, No Drawings

LOWER ALKOXYMETHYL ESTERS OF 2,4,6-TRIIODOBENZOIC ACID DERIVATIVES

BACKGROUND OF THE INVENTION

1. Field of the Invention

This invention relates to the field of organic chemistry and more particularly to novel esters useful as nonionic X-Ray contrast media.

2. Description of the Prior Art

Various derivatives of 2,4,6-triiodobenzoic acid are known to be useful as X-Ray contrast media, for example, those esters described in U.S. Pat. No. 3,795,698.

One of the disadvantages asociated with certain known contrast media is that after they are administered they are immediately absorbed by the body with a corresponding decrease in time available for radiography. Others are too hydrolytically stable and will remain in the body for extended periods of time although there is sufficient time for radiography.

Accordingly, nonionic X-Ray contrast media that remain in the body only for a sufficient time for adequate radiography would be an advancement in the art.

BRIEF DESCRIPTION OF THE INVENTION

Accordingly, the present invention is directed to compounds represented by the following formula which are useful as nonionic X-ray contrast media.

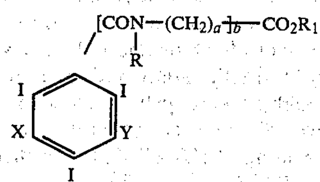

wherein, a is an integer from 1 to 3, b is 0 or 1, R is an aryl or substituted aryl, $R_1$ is (1)

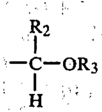

wherein $R_2$ is hydrogen or an alkyl, $R_3$ is alkyl or substituted alkyl; or (2) a cyclic glycosyl represented by the following formula;

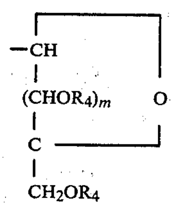

wherein $R_4$ is hydrogen or an acyl group and m is 2 or 3, X and Y are individually nonionizing functions compatible with low toxicity and/or water solubility in the 2,4,6-triiodophenyl configuration.

The novel compounds of this invention after administration to an animal or human hydrolyze at appropriate rates and are not immediately absorbed. Therefore, they remain in position in the body cavity for a sufficient time for adequate radiography. Thereafter, they hydrolyze to water-soluble nontoxic products which are excreted via usual body mechanisms. Additionally the degree of hydrolytic stablity needed can be varied depending upon the radiographic technique to be employed, e.g., lymphangiography 1 to 2 hours, bronchiography ½ to 1 hour. Lastly, the compounds of this invention are adequately stable to basic media. In other words, these compounds provide greater flexibility in terms of (a) selective biodegradation and (b) formulations.

DETAILED DESCRIPTION OF THE INVENTION

As mentioned R is an aryl or substituted aryl. Examples include phenyl and phenyl substituted with a lower alkyl radical or with an alkoxy radical containing 1 to 6 carbon atoms. Specific examples include benyl, methyl phenyl and ethyl phenyl.

$R_2$ and $R_3$ may be alkyl or substituted groups. Illustrative alkyl groups include linear or branched alkyl groups containing 1 to 10 carbon atoms. Lower alkyl groups are preferred—that is those containing 1 to 6 carbon atoms. Illustrative alkyl groups include methyl, ethyl, propyl, isopropyl, butyl, amyl, isoamyl, hexyl, heptyl, nonyl or decyl.

Illustrative substituted alkyl groups include aralkyl such as phenylalkyl containing 1 to 6 carbon atoms in the alkyl group. Specific examples include phenylmethyl and phenylethyl.

$R_4$ may be an acyl radical containing 2 to 10 carbon atoms, preferably 2 to 5 carbon atoms. Representative acyl groups include acetyl, butanoyl, pentanoyl, heptanoyl and decanoyl.

Representative cyclic glycosyl radicals include per-O-acyl-aldopentopyronasyl, and per-O-acylaldohexofuranosyl, such as, 2,3,4-tri-O-acetyl-β-D-arabinopyranosyl;
2,3,4-tri-O-acetyl-β-D-xylopyranosyl;
3,4,6-tri-O-acetyl-β-D-glucopyranosyl;
2,3,4,6-tetra-O-acetyl-α-D-glucopyranosyl, and others described on pages 214–215 of J. Stanck, et al., *The Monosaccharides*, Academic Press, New York, N.Y. 1963.

As mentioned, the substituent in the 3 and 5 positions of the ring, namely X and Y are nonionizing functions compatible with low toxicity and/or water-solubility in the 2,4,6-triiodophenyl configuration. As is known by those skilled in the art, the term "detoxifying and/or solubilizing groups" has been used as a generic designation for a substantial number of functional groups whose occurrence in the meta-position in a 2,4,6-triiodinated moiety has come to be associated with compounds which exhibit a relatively low toxicity and/or a relatively high water solubility (cf. G. B. Hoey, P. E. Wiegert and R. D. Rands, Jr., "Organic Iodine Compounds as X-Ray contrast media:, in *International Encyclopedia of Pharmacology and Therapeutics,* Section 76, "Radio-contrast Agents", P. K. Knoefel, Section Editor, Pergamon Press; Vol. 1, pp, 23–40, 54–73 (1971). While the use of such terminology originated in connection with 2,4,6-triiodobenzoic acid derivatives possessing relatively low toxicity and/or relatively high water solubility, the results set forth herein are consistent with the view that substantially the same nonionizing functions are also compatible with low toxicity and/or water solubility in the tiiodinated moiety of the nonionic compounds of the present invention. Furthermore the compounds of this invention do undergo hydrolysis to non-toxic, water-soluble X-ray contrast media.

Among the nonionizing functions which may constitute X and Y may be mentioned the following: lower alkoxy, e.g., methoxy and ethoxy; hydroxy-(lower alkoxy), e.g., 2-hydroxy-ethoxy; lower alkoxy-(lower alkoxy), e.g., methoxy-ethoxy and ethoxy-propoxy; lower acylamino, e.g., acetamido and propionamido; lower acylamino-(lower alkyl), e.g., acetamidomethyl and acetamidoethyl; lower acylamino-(lower acylamino), e.g., aceturamido; hydroxy-lower acylamino, e.g., hydroxyacetamido and hydroxy-propionamido; N-(lower alkyl)-lower acylamino, e.g., N-methylacetamido and N-methyl-propionamido; lower alkylsulfonamido, e.g., methylsulfonamido and ethylsulfonamido; N-(lower alkyl)-lower alkylsulfonamido, e.g., N-methylethylsulfonamido and N-ethyl-methylsulfonamido; 3,3-bis(-lower alkyl)-ureido, e.g., 3,3-dimethylureido and 3-methyl-3-ethylureido; lower perfluoroacylamino, e.g., perfluroacetamido and perfluoropropionamido; carbamyl; N-(lower alkyl) carbamyl, e.g., N-methylcarbamyl and N-ethylcarbamyl; N,N-di-(lower alkyl) carbamyl, e.g., N,N-dimethylcarbamyl and N,N-diethylcarbamyl; lower alkoxy-(lower acylamino), e.g., methoxyacetamido and ethoxyacetamido; lower alkoxy-alkoxy-(lower acylamino), e.g., methoxy-ethoxy(acetamido); hydroxy and hydroxy-lower alkyl, e.g., hydroxy-methyl and hydroxyethyl. As used herein, the term "lower" (e.g., lower alkyl and lower alkoxy) means that the function contains between 1 and 6 carbon atoms. These skilled in the art will recognize that functions of the above type other than those specifically enumerated may also constitute X and Y.

Representative compounds of this invention include
Butoxymethyl 3-Acetamido-2,4,6-triiodobenzoate;
Heptoxymethyl 3-Acetamido-2,4,6-triiodobenzoate;
1-Ethoxyethyl 3-Acetamido-2,4,6-triiodobenzoate;
1-Hexoxypropyl 3-Acetamido-2,4,6-triiodobenzoate;
Propoxymethyl 3-Acetamido-2,4,6-triiodo-N-methylisophthalamate;
1-Pentoxyethyl 3-Acetamido-2,4,6-triiodo-N-methylisophthalamte;
Octaoxymethyl 3-Acetamido-2,4,6-triiodo-N-methylisophthalamate;
2,3,4,6-tetra-O-propanoyl-glucopyranosyl 3-Acetamido-2,4,6-triiodo-N-methylisophthalamate;
2,3,5,6-tetra-O-acetyl galactafuranosyl 3-Acetamido-2,4,6-triiodo-N-methyl isophthalamate;
2,3,5,6-tetra-O-acetyl arabinopyranosyl 3-Acetamido-2,4,6-triiodo-N-methyl isophthalamate;
1-Ethoxyethyl 3-(3-Amino-2,4,6-triiodo-N-phenylbenzamido)propionate;
Butoxymethyl 3-(3-Amino-2,4,6-triiodo-N-phenylbenzamido)propionate;
1-Hexoxyethyl 3-(3-Amino-2,4,6-triiodo-N-phenylbenzamido)propionate.

The above mentioned novel compounds may be prepared by reacting an $\alpha$-halo acylic or cyclic ether with the appropriate triiodobenzoic acid derivative. $\alpha$-bromo or $\alpha$-chloro ethers are preferred. Such a reaction is straightforward as will be appreciated by those skilled in the art and need not be described in more detail here.

The novel compounds of this invention may be used as X-ray contrast agents in various radiographic procedures including those involving bronchiography, lymphography, gastrointestinal radiography, myelography, hepatography and urography. They are relatively water insoluble but can hydrolyze in vivo at various rates to provide non-toxic, water soluble, X-ray contrast media (as well as other products) which are safely and rapidly excreted by the normal mechanisms for such compounds, for example, in bronchiography.

The following examples illustrate the invention.

EXAMPLE I

Preparation of Ethoxymethyl 3-Acetamido-2,4,6-triiodobenzoate

A. Preparation of Chloromethyl Ethyl Ether

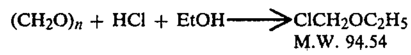

Essentially, the procedure of J. Farren, H. Fife, F. Clark & C. Carlard, *J. Am. Chem. Soc.*, 47, 242 (1925) was used.

Paraformaldehyde (1 lb., 15.08 gram-moles of $CH_2O$) and 100% ethanol (696 g., 15.08 mole) were slurried in a 3-liter, three-necked flask equipped with a stirrer, gas inlet tube, thermometer, condenser and drying tube. The reaction was stirred and cooled in an ice bath and anhydrous hyrogen chloride (692 g.) was passed in until all the paraformaldehyde had dissolved. The layers were separated and the organic layer was dried over $CaCl_2$ for $1\frac{1}{2}$ hours. The $CaCl_2$ was filtered and dry nitrogen was bubbled through for $1\frac{1}{2}$ hours to drive out excess HCl. The crude chloromethyl ether was distilled rapidly without fractionation and with dry nitrogen bubbling through continuously. During the distillation, some paraformaldehyde collected in the condenser. The fraction boiling at 79°–82° C. was redistilled in the same manner. The material boiling at 82°–92° C. was fractionally distilled through a 20-in. column packed with helices. Three fractions were obtained:

I. BP 70°–81°; $n_D^{26.2}$ 1.4000,
II. BP 81°–82° ; $n_D^{25.5}$ 1.4007,
III. BP 82°–83°; $n_D^{26}$ 1.4007, [Farren, Loc. cit., b.p. 81°–82°; Littershield, Ann., 330, 122(1904), b.p. 83°, $n_D^{20}$ 1.4040; L. S. Summers, *Chem. Revs.*, 55, 304 (1955), b.p. 84°, $n_D^{18}$ 1.4040].

Fractions II and III totaled 692.9 g. (yield 48.7%). The liquid was stored over $CaCO_3$ to consume any HCl evolved and thus retard decomposition.

B. Preparation of Ethoxymethyl 3-Acetamido-2,4,6-triiodobenzoate

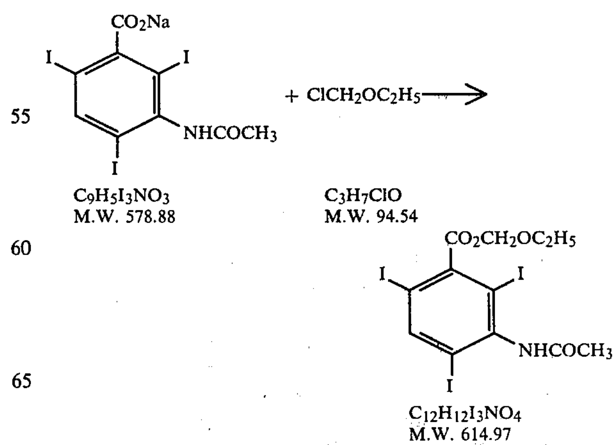

To a stirred slurry of sodium 3-acetamido-2,4,6-triiodobenzoate (14.5 g, 0.025 mole) in dimethylformamide (150 ml) was added chloromethyl ethyl ether (2.56 g, 0.027 mole). A white solid (NaCl) precipitated promptly. The mixture was stirred overnight, filtered, and evaporated to near dryness under reduced pressure to yield 17.8 g. of residue. The residue was dissolved in 200 ml. of chloroform, filtered and the filtrate was extracted with 5% aqueous sodium bicarbonate, washed with water and dried over anhydrous sodium sulfate and evaporated under reduced pressure to dryness. The residue (10.5 g.) obtained was recrystallized from carbon tetrachloride (200 ml.) and chloroform (enough to dissolve the residue), to yield the product 5.05 g. (31.5%), m.p. 174°-177.7° C. The ir and and nmr spectra were in agreement with the structure as assigned.

Anal. Calcd. for $C_{12}H_{12}I_3NO_4$: C, 23.43; H, 1.97; I, 61,91; N, 2.28.

Found: C, 23.42; H, 1.91; I, 62.20; N, 2.26.

EXAMPLE II

Preparation of Ethoxymethyl 3-Acetamido-N-methyl 2,4,6-triiodoisophthalamate

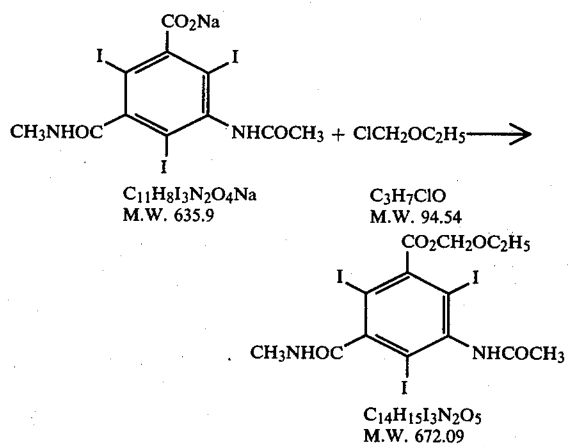

Chloromethyl ethyl ether (102.6 g., 1.09 moles, 100 ml.) was added in 5 minutes to a stirred solution of the sodium salt of iothalamic acid (635.9 g., 1 mole) in 6 l. of dimethylformamide. Some fumes were evolved and there was an immediate precipitate. After stirring for about 1.5 hours dimethylformamide was removed under reduced pressure. The residue was dissolved in 6.5 l. of chloroform and 1.5 l. of dimethylformamide and was extracted twice with 4 l. of 5% aqueous sodium bicarbonate. The chloroform layer was dried over sodium sulfate and magnesium sulfate overnight and the solvent was removed under reduced pressure. Yield was 433.1 g. of nearly pure product.

The crude product was recrystallized from 250 ml. of dimethylformamide and 4600 ml. of carbon tetrachloride to yield 242 g. (36%) of product, decomposes 275°-280° C. Tlc showed a single spot with a trace of iothalamic acid; ir and nmr spectra confirmed the structure.

Anal. Calcd. for $C_{14}H_{15}N_2I_3O_5$: C, 25.01; H, 2.25; N, 4.17; I, 56.66. Found: C, 25.17; H, 2.35; N, 4.25; I, 56.35.

EXAMPLE III

Preparation of Ethoxymethyl N-(3-Amino-2,4,6-triiodobenzoyl)-N-phenyl-3-aminopropionate

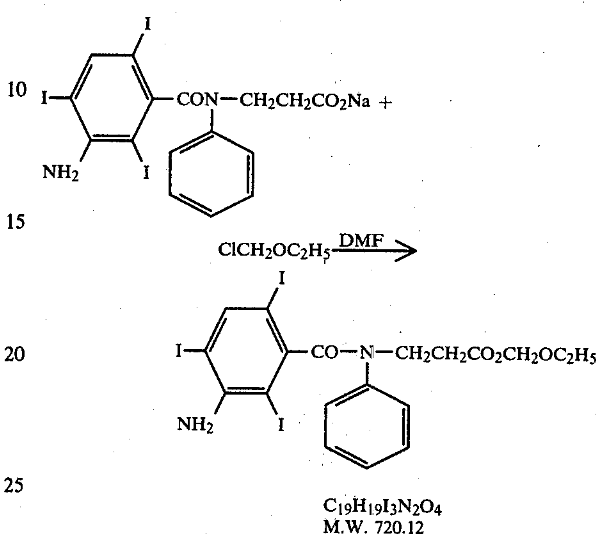

Sodium ethoxide was prepared from 1.74 g. (0.0756 g-atom) of sodium in 2B ethanol (250 ml.). Iobenzamic acid (50 g., 0.0756 mole) and 250 ml. of 2B ethanol were added. After the iobenzamic acid dissolved, the solution was evaporated to dryness under reduced pressure. An orange color developed during heating. The residue was dissolved in 500 ml. of dimethylformamide and some of the dimethylformamide (75 ml.) was evaporated (vacuum pump) to entrain any residual ethanol. The solution was cooled to 1.5° C. and chloromethyl ether (0.076 g., 7.2 ml.) was added in one portion. The temperature rose to 4.5° C., the red-brown color changed to a rose color and a precipitate formed (the precipitate later redissolved). The thin-layer (benzene-MEK-methanol, 60:25:10) chromatogram of this reaction product versus iobenzamic acid showed a new spot with a slightly greater $R_f$ than iobenzamic acid. Some unreacted iobenzamic acid was present. Dimethylformamide was evaporated (vacuum pump), the residue was dissolved in chloroform (100 ml.), and extracted with 300 ml. of 5% sodium bicarbonate. Dimethylformamide (200 ml.) was added and the extraction was repeated. Tlc confirmed the nearly complete removal of iobenzamic acid. All solvents were evaporated (vacuum pump). The residue (45 g.) was extracted with 700 ml. of ether. A brown insoluble residue was rejected. Petroleum ether was added to ether solution until it was turbid.

After overnight stirring, a first crop of 26.00 g. (48%), m.p. 125°-127° C., was collected. A thin-layer of this material in two systems (benzene, methyl ethylketone, acetic acid (60:25:10); chloroform isopropanol, ammonium hydroxide (60:30:10) indicated it was free of unreacted iobenzamic acid. The product was recrystallized from tetrahydrofuran-pet ether to yield 19.1 g., m.p. 129°-132.5° C. The nmr and ir confirmed the structure.

Anal. Calcd. for $C_{19}H_{19}I_3N_2O_4$: C, 31.69; H, 2.66; I, 52.87; N, 3.82.

Found: C, 31.77; H, 2.71; I, 53.21; N, 3.79

EXAMPLE IV

Preparation of 2,3,4,6-tetra-O-acetyl-α-D-glucopyranosyl 3-Acetamido-2,4,6-triiodo-N-methylisophthalamate

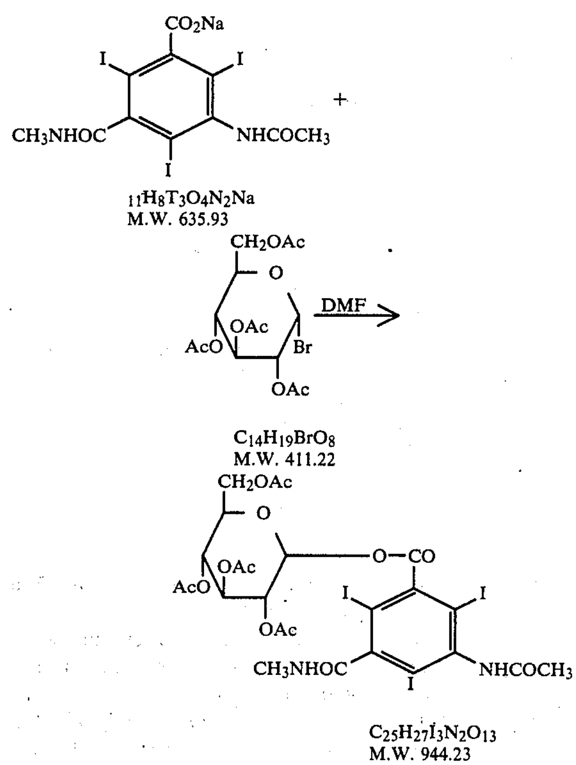

Sodium iothalamate (41.3 g., 0.065 mole) was dissolved in 400 ml. of dimethylformamide. Tetraacetylglucosyl bromide (26.7 g., 0.067 mole) was added in one portion. There was no temperature rise. The course of the reaction was followed by thin-layer chromatography (system-benzenemethyl ethyl ketone-acetic acid 60:25:10). Aliquots were taken from the dimethylformamide reaction mixture, diluted with tetrahydrofuran and spotted versus a zero time sample of sodium iothalamate. After one hour stirring at room temperature, a single large spot with an $R_f$ greater than Na iothalamate appeared (TLC system, 60 parts benzene—25 parts methyl ethyl ketone—10 parts acetic acid). The thin-layer chromatogram did not change after stirring overnight at room temperature or 1½ hours at 80° C. The dimethylformamide was evaporated (vacuum pump) leaving a glassy, foam-like residue. The residue was dissolved in 150 ml. of dimethylformamide and 375 ml. of chloroform and extracted with 360 ml. of 5% aqueous bicarbonate. The organic layer was separated immediately, dried with sodium sulfate overnight, and concentrated under reduced pressure leaving a residue of 48.8 g. Thin-layer chromatography of this showed only a trace of iothalamic acid left (TLC system, benzene-methyl ethyl ketone-acetic acid, 60:25:10). The residue was crystallized from 100 ml. of chloroform and 300 ml. of carbon tetrachloride to yield a 1st crop of 20.5 g. and 2nd crop of 12.2 g. (TLC using the same system as above was identical with the 1st crop). Both crops were combined (30.6 g.) and recrystallized from 100 ml. of THF and 250 ml. of ether, yield 17.4 g., m.p. 171°–178° C. (dec). The ir and nmr were in accord with the proposed structure.

Anals. Calcd. for $C_{25}H_{27}I_3N_2O_{13}$: C, 31.80; H, 2.88; I, 40.32; H, 2.96. Found: C, 32.03; H, 3.02; I, 39.38; N, 2.73.

EXAMPLE V

In order to study the hydrolytic stability of Example I, a 1 gram sample was rolled with 75 ml. of phosphate buffer solution (pH 7.4) and glass beads (to increase the surface area) for 16.5 hours. The pH fell to 3.49. This demonstrated the aqueous instability of the ethoxymethyl ester linkage at physiological pH. A 1 gram sample of Example II was treated in the same manner. After 16.5 hours of rolling in pH 7.4 phosphate buffer, the pH had fallen to 2.56. The sample of Example II had virtually all dissolved, indicating complete hydrolysis.

EXAMPLE VI

½ gram of each of Example II, Example III and Example IV were rolled 24 hours in 40 ml of pH 7.46 phosphate buffer solution with glass beads. The results are tabulated below. The slurries were examined by thin-layer chromatography (System chloroform-isopropyl alcohol-ammonium hydroxide, 60:30:10).

TABLE I

| Compound | Initial pH | After 24 hrs. | Appearance | TLC of Slurry |
|---|---|---|---|---|
| Example III | 7.40 | 7.48 | Milky slurry | No decomposition |
| Example IV | 7.42 | 7.38 | Milky slurry | Trace of iothalamic acid |
| Example II | 7.2 | 3.72 | Dissolved | All iothalamic acid |

EXAMPLE VII

A metabolism study was run on Examples II, III, and IV by intraperitoneally injecting 5–6.5 ml. of the Examples into rats. Radiographically, contrasts disappeared in 10 days for Example II, 35 days and 15 days for Example IV.

EXAMPLE VIII

The $LD_{50}$ for Examples I–IV was determined by intraperitoneally injecting the example compounds into mice. For Example I it was 3119 mg/kg and small amounts of the compound were found in the abdominal cavity at necropsy. For Example II, it was 16,000 mg/kg±977 and traces of the compound were found in the peritoneally cavity at necropsy. For Example III and IV they were greater than 10,000 mg/kg.

EXAMPLE IX

An excretion study was determined for Examples I and II by injecting compunds of Examples I and II (equivalent to 500 mg/kg of $I_2$) intraperitoneally into 3 small rats. For Example I, 71.27% of the iodine injected was recovered over a 96 hour period in urine, feces and the peritoneally washings obtained at necropsy. Most excretion occurred in 48 hours. At necropsy some adhesions of the intestines and some liver damage was evident. For Example II, 73.6% was recovered over a 96 hour period with most of the excretion occurring in 48 hours. At necropsy some adhesions of the intestines and some liver damage was evident.

EXAMPLE X

A lymphogram of a dog was made after injecting two milliliters of Example I subcutaneously and 9.6 milliliters intraperitoneally. Poor to moderate visualization resulted. Another lymphogram of a dog was made after injecting 2.5 grams intralymphatically. Six x-rays were taken. No contrast medium passed at the first (popliteal) node in 24 hours at which time the dog was sacrificed.

EXAMPLE XI

A lymphogram of a dog was made after injecting 5 milliliters of Example II subcutaneously. Poor to moderate visualization resulted. In another lymphogram 2 milliliters of Example II was injected intralymphatically into the right side and 1 ml. into the left side of a dog. The contrast medium did not pass the popliteal lymph node.

EXAMPLE XII

A bronchogram of a dog was made after administering Example III in powder form via a Murphy endotracheal tube using a DeVilbiss powder blower, oxygen tank and polyethylene tube. The opacity and homogenity was poor and the coating was fair. In another study 3 gms of powder gave poor to fair opacity lasting at least 2 hours. Less than one gram was retained in the lungs.

As various changes could be made in the above invention without departing from its scope it is to be understood therefore that the invention is not limited except as defined by the appended claims.

What is claimed is:

1. A compound represented by the following formula:

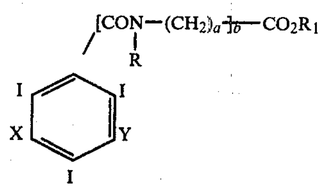

wherein a is an integer from 1 to 3, b is 0 or 1, R is phenyl, $R_1$ is

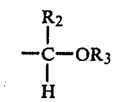

wherein $R_2$ is hydrogen and $R_3$ is lower alkyl and X and Y are individually nonionizing functions compatible with low toxicity and/or water solubility in the 2,4,6-triiodophenyl configuration selected from the group consisting of hydrogen, lower acylamino, carbamyl, N-(lower alkyl)carbamyl and amino at least one of X and Y being other than hydrogen.

2. Ethoxymethyl 3-Acetamido-2,4,6-triiodobenzoate.

3. Ethoxymethyl 3-Acetamido-N-methyl-2,4,6-triiodoisophthalamate.

4. Ethoxymethyl 3-(3-Amino-2,4,6-triiodo-N-phenylbenzamido)-propionate.

* * * * *